(12) United States Patent
Chibret et al.

(10) Patent No.: US 6,336,571 B1
(45) Date of Patent: Jan. 8, 2002

(54) DEVICE FOR PACKAGING A LIQUID TO BE DISPENSED DROP BY DROP

(75) Inventors: Henri Chibret, Joze; Michel Faurie, Veyre-Monton; Jacques Luyckx, Ceyrat; Alain Defemme; Thierry Coquel, both of Chamalieres, all of (FR)

(73) Assignee: Laboratoires Thea S.A., Clermont-Ferrand (FR)

( * ) Notice: Subject to any disclaimer, the term of this patent is extended or adjusted under 35 U.S.C. 154(b) by 0 days.

(21) Appl. No.: 09/530,650
(22) PCT Filed: Nov. 4, 1998
(86) PCT No.: PCT/FR98/02353
§ 371 Date: May 3, 2000
§ 102(e) Date: May 3, 2000
(87) PCT Pub. No.: WO99/23006
PCT Pub. Date: May 14, 1999

(30) Foreign Application Priority Data

Nov. 4, 1997 (FR) .......................................... 97 13863

(51) Int. Cl.$^7$ ................................................ B67D 5/58
(52) U.S. Cl. ............. 222/189.09; 222/187; 222/189.06; 222/190; 222/209; 222/183
(58) Field of Search ................................ 222/206, 209, 222/187, 189.06, 189.09, 190, 183

(56) References Cited

U.S. PATENT DOCUMENTS

| 3,669,323 A | | 6/1972 | Harker et al. |
| 4,634,023 A | | 1/1987 | Tanaka et al. |
| 5,105,993 A | * | 4/1992 | La Haye et al. ............ 222/189 |
| 5,310,085 A | * | 5/1994 | Lontrade et al. ............... 222/1 |

FOREIGN PATENT DOCUMENTS

| DE | 19618750 | 11/1996 |
| EP | 425264 | 5/1991 |
| WO | 9005110 | 5/1990 |

* cited by examiner

Primary Examiner—Kevin Shaver
Assistant Examiner—Stephanie Willatt
(74) Attorney, Agent, or Firm—Millen, White, Zelano & Branigan, P.C.

(57) ABSTRACT

The invention concerns a device comprising a flask (1) with variable internal volume having a rigid neck (5) wherein is arranged the body (3) of a dispensing head (2) ending in a conduit (41) discharging the liquid and containing a microporous pad (6) for generating a head loss regulating the liquid flow pushed therethrough into a distribution chamber (31) communicating with said conduit. The pad is advantageously made of a material inert with respect to the liquid and combined with an antibacterial filtering element (9) preventing outside air from entering the flask. It evenly occupies the body (3) over the whole cross-section of the liquid passage.

20 Claims, 2 Drawing Sheets

DEVICE FOR PACKAGING A LIQUID TO BE DISPENSED DROP BY DROP

The present invention relates to the liquid-packaging industry, more particularly where the issue is one of designing and manufacturing containers with built-in stopper/dispensers used for packaging liquids that are to be dispensed drop by drop.

Devices of this kind have many fields of application, not only in the world of pharmaceutical or cosmetic products but also, for example, in the case of lubricants or solutions used in the agri-foodstuff industry. The main aim in using them is to keep liquid products which are used only gradually in small amounts for as long as possible, by expelling just a few drops each time.

Very often, the product kept in the flask has also to be protected from any contamination. This is the case, for example, with ophthalmic solutions, that have to be kept away from the ambient air and the bacteria it contains. In practice, the preserving of such solutions follows two routes, which may, incidentally, be used simultaneously. One of these consists in placing an anti-bacterial filter over the conduit through which the drops are expelled, and the other consists in incorporating a preservative into the liquid which has then to be held back so as to rid the expelled product of it.

In the prior art to the present invention, there are known devices for packaging liquids that are to be dispensed drop by drop which comprise a flask, the interior volume of which can be varied by manually deforming its walls, and a dispensing nozzle containing a purifying element inserted in the path taken by the liquid as it is expelled from the flask under the effect of the pressure exerted by reducing the volume of the latter.

Such packaging devices are described, for example, in French Patent 2,638,428 in the name of the applicant. It may be seen in that patent that, in the dispensing nozzle, the conduit for expelling the liquid is preceded by a lock chamber bounded by a purification element upstream, this being capable of holding back the preservative in an ophthalmic solution that constitutes the liquid that is to be dispensed, and by a filtration element downstream, consisting, for example, of an anti-bacterial membrane.

However, the known devices have even more drawbacks to which the present invention affords a solution. When, in particular, they are used for treating disorders of the eye, the liquid needs to be instilled into the eye of the patient drop by drop, and this operation is all the more tricky as it is commonly performed by the patient himself.

More generally, these devices do not give the desired precision in the correct metering of the product. On the one hand, it is difficult to exert the desired slow and uniform repetitive expulsion pressure and if, for example, when pressing on the outer wall of the flask, one presses too quickly, one does not manage to form drops and too much product is expelled in one shot. Furthermore, the pressure to be exerted by the user varies in the course of the use of the device. It increases as the product is used up, and at the end of the useful life, there is still a dead volume of unusable liquid left inside the flask.

The invention therefore aims to be able to obtain a low and uniform liquid delivery rate as is desirable for the formation of drops, at the same time escaping the influence of the conditions under which the deformable walls of the flask are manipulated so that the dispenser can truly operate as a dropper. It also aims to allow fuller use of the product initially introduced into the flask.

Through its various features, as will be defined and described hereinafter and as may advantageously be applied on an industrial scale, the invention does not only provide control over the formation and ejection of individual drops but also allows the operating security of the packaging device to be improved in terms of its other functions such as the degree of purity of the product, makes it easier to manufacture on an industrial scale and allows cost to be reduced.

In order to achieve its various objectives, the invention proposes a device for packaging a liquid that is to be dispensed drop by drop, comprising a flexible-walled flask that can be deformed manually to gradually decrease its internal volume towards a rigid neck in which is mounted a dispensing head ending in a conduit for expelling the liquid out of the flask, characterized in that this device comprises a microporous pad inserted in the body of the dispensing head across the cross-sectional area for the passage of the liquid between the flask and the expulsion conduit upstream of a liquid-distribution chamber formed between a downstream face of the pad and the expulsion conduit.

This pad has the effect of creating a head loss which regulates the flow of liquid driven through it by the pressure generated in the flask as its volume is reduced. The dose which passes through it each time the user exerts a compressive action on the flask collects in the buffer volume of the distribution chamber before leaving via the expulsion conduit in the form of clearly distinct drops. On this subject, it would seem that the device according to the invention is capable of operating particularly well when the distribution chamber has a large enough volume to accommodate a dose of one to three drops of liquid.

A microporous pad which proves satisfactory according to the invention is advantageously made of a material which is inert with respect to the liquid contained in the flask. Appropriate materials will, in particular, be felts or foams with highly porous open pores such as can be obtained in known ways from various organic polymer resins. In the main applications of the invention, it is advantageous for the microporous pad to be made in the form of a pellet of polyester resin or modified polyester resin felt, such as, in particular, low-density polyethylene resins or polyether sulphone resins.

Resins of this type or the equivalent, which are of course known per se, have the benefit, in the context of the invention, of lending themselves to the production of a cylindrical pad, with diameters from 0.5 to 3 cm and lengths of between 0.2 and 1 cm, with sufficient flexibility that they can be leaktightly force-fitted into the, advantageously cylindrical, body of the dispensing head and can offer, for the passage of the liquid in the longitudinal direction, microducts with a mean pore diameter that can be chosen from between 0.3 and 10 microns.

The above ranges of sizes are particularly suited to affording the desired effect in the case, in particular, of aqueous medicinal solutions, such as solutions for treating the cornea or any other solution intended to be administered to the eye as drops.

In a lock chamber as mentioned hereinabove with regard to the prior art illustrated by the French patent in the name of the applicant published under the Ser. No. 2,638,428, the pad of the device of the invention is configured and arranged in such a way that it occupies the said lock chamber over its entire cross-sectional area and preferably does so over one to two thirds of its longitudinal height, the remainder of this height being reserved for the distribution chamber.

Combining the said pad with a downstream filtration element of an anti-bacterial membrane type is also advantageous, for protecting the liquid contained in the flask and preventing it from becoming contaminated from the ambient air. A particularly well-suited membrane commonly has a thickness of a few tenths of a millimetre and a mean mesh size of between 0.2 and 0.8 microns. When impregnated with solution, it prevents ambient air from entering the flask to replace the liquid expelled. It is therefore clear that, in itself, the pad recommended by the invention is completely different from this both in terms of its structure and in terms of its function.

In combination with the presence of a downstream filtration or purification element advantageously consisting of an anti-bacterial membrane, the invention has as a secondary feature the fact that this element is arranged pressed against a nozzle connected to the body of the dispensing head in which the expulsion conduit is formed. In practice, it should be understood here that the membrane is held flat between two plates which are nevertheless perforated, so as to prevent any liquid remaining between two dispensing steps and damping the membrane, as this would detract from its operation.

By way of a preferred example, a plate of this kind may be made of the material of the dispensing head by fins in a star configuration forming a separator between the downstream face of the microporous pad and the anti-bacterial membrane. In collaboration with these fins, the nozzle will advantageously have grooves set out as concentric annular sectors around a central orifice of the expulsion conduit.

Incidentally, the dispensing head, constituting an insert or pod in the neck of the flask, may additionally bear another purification element located upstream of the microporous pad, particularly an element which is conventional in itself and intended to rid the expelled liquid of a preservative, which is then held back in the flask as desirable, for example, in the case of ophthalmic solutions. In accordance with other embodiments of the device of the invention, the same pad may combine a number of the above functions. This will, in particular, be the case if the pad has a layer of coating or appropriate treatment on its upstream face.

In any event, the regulation afforded by the pad of the device of the invention on the stream of liquid driven through it, preventing exaggerated overpressures from manifesting an effect beyond the flask itself, allows the imposition of the pressure difference between the inside of the flask and the outside to be the one best suited to the formation of drops. However, it would also seem that the distribution of liquid passing uniformly along the microducts across the entire cross-sectional area of its path before collecting in the distribution chamber upon leaving the pad makes a great contribution to the beneficial effect afforded by the invention.

Other features of the invention are directly associated with the foregoing in so far as the improved conditions under which the drops are formed allow the construction of the device as a whole to be better suited to the practical requirements in varied sizes and capacities and allow it to be manufactured more easily at lower cost.

According to one of the embodiments of the device of the invention, the wall of the flask is of cylindrical overall shape in the form of a longitudinally deformable bellows ending in a rigid transverse bottom. It is advantageously made as a single piece of material that can be moulded with the rigid neck for the mounting of the dispensing head and with an outer reinforcing ring protruding radially from the overall size of the bellows so as to allow it to be grasped by an automatic assembly machine without touching the more delicate wall of the said bellows.

Provision is advantageously made for such a bellows-type flask to be mounted via its neck inside a protective outer casing which envelopes it over most of its length. The above outer ring is then extremely useful for carrying out an assembly process which consists in forcibly pushing the flask into this casing by handling it using a tube in abutment against the ring.

When it is desirable for the bellows wall to be compressible over practically all of its length, a very suitable solution consists in giving the casing that protects the bellows a length at least equal to that of the uncompressed bellows while at the same time equipping it with a slot for access from its open bottom.

However, the invention gives preference over this solution to the solution whereby the said casing has a continuous cylindrical periphery and is associated with a closure cover which fits onto it as a continuation thereof, and is removable to give access to the bottom of the flask. This not only has the advantage of affording better protection to the flexible flask, but also has the advantage of being better suited to automated manufacture with the affixing of adhesive labels stuck around the cylindrical casing.

The invention will now be more fully described in the context of its preferred features and their advantages with reference to the figures of the appended drawings which illustrate them and in which.

Figure 4:
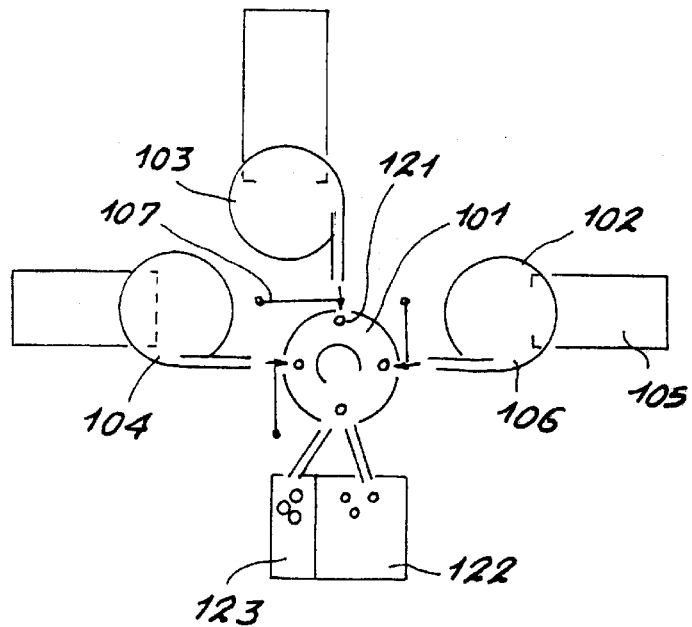
Figure 5:
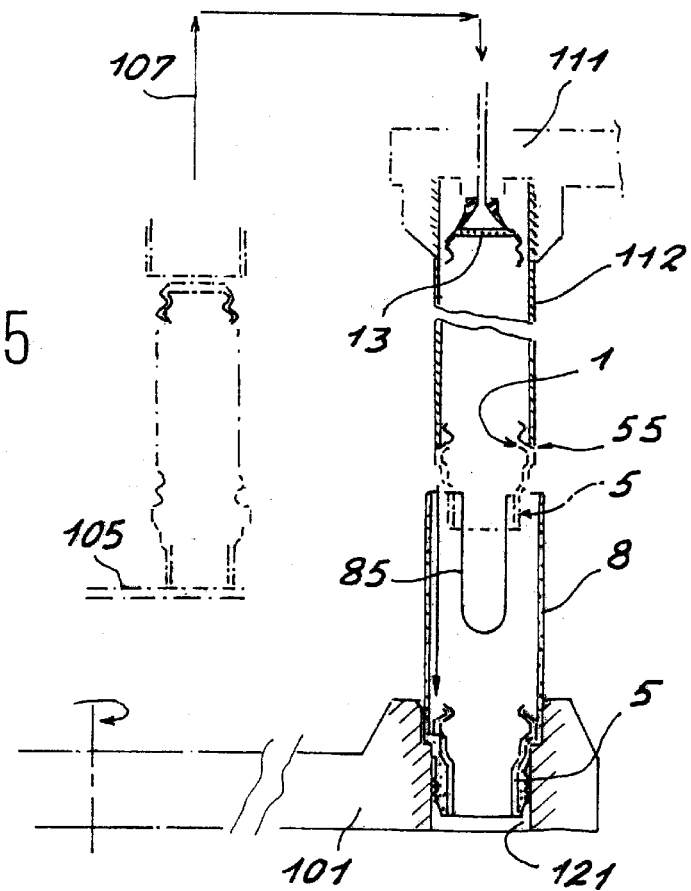

FIG. 4 diagrammatically shows the main work stations of a machine for assembling the various parts of the device in mass production; and FIG. 5 illustrates the state of placing the bellows in its casing that the assembly method employed using such a machine includes.

The packaging device described is such that it is particularly suited to aqueous liquids that are to be dispensed drop by drop, and more specifically pharmaceutical solutions in aqueous medium such as so-called eye drop solutions.

It comprises a container for containing the liquid, consisting of a flask 1 which opens in the form of a neck 5, a protective outer casing 8 around this flask, a dispensing head 2, the body 3 of which forms a pod which can move between two positions in the neck 5 of the flask, and a nozzle 4 which completes this body outside the flask and is pierced with an expulsion conduit 41. A removable cap 7 is fitted over the assembly.

The interior volume of the flask 1 can be varied by manual action by deforming its walls. It can be seen from the figures that, over most of its longitudinal part along the axis of the device, vertically in the position depicted, its wall is of cylindrical overall shape in the form of a bellows 12 that can be compressed, thus reducing its length. More specifically, and as is apparent in particular from FIG. 2, in order to achieve this, the user actuates a rigid bottom 13 of the bellows 12, which he pushes with a finger (generally the index finger when holding the flask by its head between his thumb and his middle finger) towards the neck of the flask and the associated dispensing head. The resulting reduction in volume occurs gradually, in discrete stages upon each drop-by-drop dispensing operation in so far as the device is equipped with means that prevent the outside air from entering the flask to replace the liquid expelled.

This last capability is conferred upon it, in the preferred embodiment described here, by an anti-bacterial membrane 9 which is held flat between two support plates across the entire cross-sectional area for the passage of the liquid in the body 3 of the dispensing head. It is also arranged in such a way that it never stays wet with the liquid from the flask outside of periods of use for drop-by-drop dispensing. This allows the efficacy of the membrane in its anti-bacterial and air-impermeable activity to be preserved throughout the shelf life and useful life of the flask. A membrane such as this, conventional in itself, has a mean pore size of 0.45 microns, for example.

According to the invention, a microporous pad 6 is inserted in the body 3 of the said dispensing head 10 across the cross-sectional area for the passage of the liquid between the flask 1 and the expulsion conduit 41. This pad consists of a length of cylindrical rod made of a neutral material which is chemically inert with respect to the liquid to be dispensed contained in the flask in terms of all its ingredients, therefore including, for example, being inert with respect to a preservative contained in an ophthalmic solution. More specifically, in the example described, this is an organic material based on a polyethylene resin, which has a certain elastic flexibility so that it is easy to mount leaktightly in the dispensing head by forcibly inserting it into its body 3, witht the proviso that the latter have a cylindrical internal cross section of the same diameter without clearance.

Figure 1:
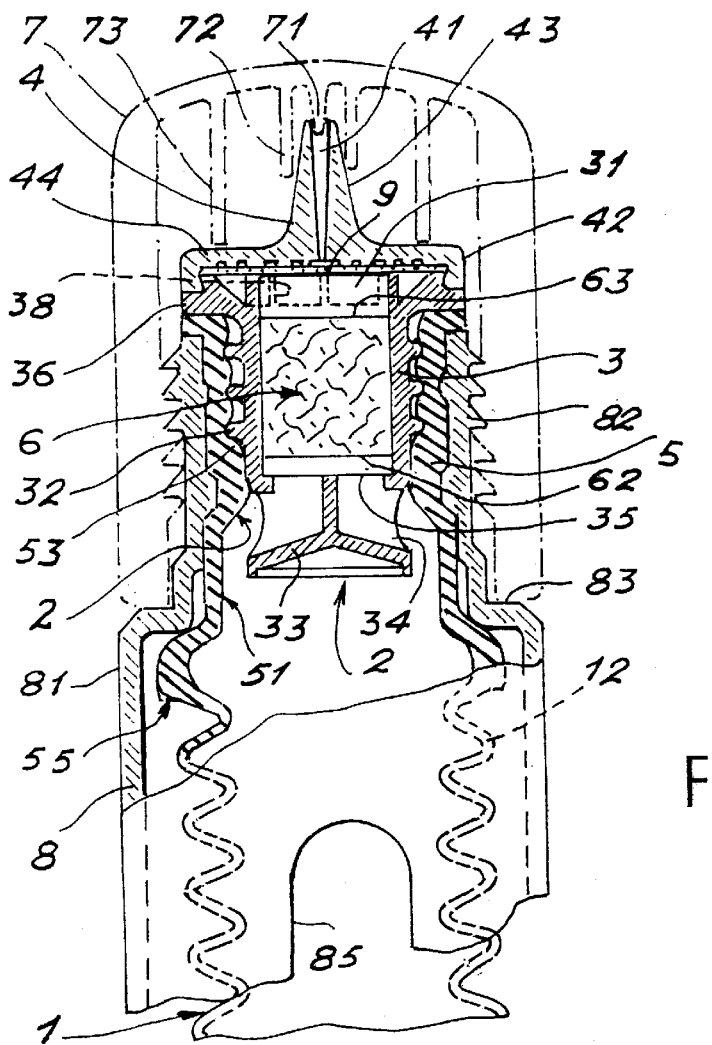
FIG. 1 depicts a device for packaging aqueous liquids according to the present invention and shows a sectional view of the upper part thereof in the region of the dispensing head.

It can be seen in FIG. 1 that the pad 6 does not extend longitudinally as far as the internal mouth of the expulsion conduit 41. On the contrary, it is arranged upstream of a chamber 31 formed in the cylindrical body 3 between a downstream surface 63 which ends the pad 6 and the terminal face of the nozzle 4. This chamber therefore has a large cross section by comparison with the expulsion conduit 41, and in actual fact is at least as wide as the cross section of the pad 6, and even a bit larger as illustrated in FIG. 1. It acts as a chamber for distributing the liquid driven by the user through the pad in so far as, as described, it has a large enough volume to accommodate the liquid which has thus passed through the pad 6, in a quantity that corresponds to a dose to be dispensed.

In the particular example described, it is allowable for the pad 6 to occupy almost two thirds of the longitudinal height of the body 3 situated in register with the neck 5 from the time of first use of the device, the remaining height being reserved for the distribution chamber 31 as far as the base of the nozzle 4 which at its centre is pierced with the orifice of the expulsion conduit 41. The microporous material has a mean pore size of the order of 0.5 microns.

Thus formed and arranged, the pad 6 is able to create a head loss that regulates the flow of liquid driven through it by the pressure generated in the flask 1 during each action to reduce its volume. Together with the chamber 31, which collects the liquid to distribute it towards the inlet of the conduit 41, and also with the way in which the bellows works, it plays a part in ensuring true drop-by-drop dispensing, by determining a pressure differential on expulsion which is now practically insensitive to the way in which the user presses on the bottom of the bellows to compress it, whether this be fast or slow exerting great or little force.

In terms of a flask designed for a pharmaceutical product, this product needs to be isolated from any possibility of contamination throughout its shelf life prior to first use. For this purpose, the device of the invention is designed to allow sealed closure between the dispensing head and the inside of the bellows 12, this at the same time having the benefit of preventing any liquid from flowing as far as the anti-bacterial membrane, whatever position the flask might be in.

Figure 3:
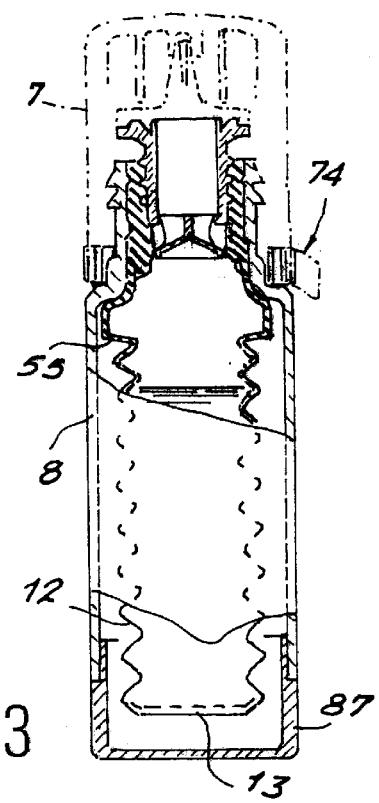
FIG. 3 illustrates an alternative form of the previous device, which differs from the latter in the construction of the outer casing which protects the bellows flask.

This sealed closure involves the configuration of the dispensing head in combination with that of the neck of the flask, plus the collaboration between the removable cap 7 and the outer casing 8, according to the embodiment illustrated more specifically in FIGS. 1 and 3.

As shown in particular in FIG. 1, the dispensing head 2 is mounted, via its body 3 which can move in the rigid neck 5 of the flask, between two predetermined positions. In each of these positions the body 3 remains leaktight in the way in which it is mounted in the neck 5, by virtue of three runs of beading 32 which it has projecting in an annulus on its periphery and which are housed elastically in corresponding annular recesses formed in the internal surface of the neck 5 in the form of grooves located longitudinally one after the next.

Prior to first use, the dispensing head is in the uppermost so-called security position illustrated in FIG. 3, two of the runs of beading 32 lying in two grooves of the neck 5, while the third (upper) merely lies along the end of the neck 5. In this position, a bottom cup 33 which is part of the body 3 is in sealed contact with the interior surface of this neck, along a frustoconical surface which forms a seat 52 for it around the axis of the device. The cup 33 therefore leaktightly seals the inside of the flask 1, and the liquid it contains cannot flow towards the pad 6.

When, on the other hand, the dispensing head is pushed downwards, into the position illustrated in FIG. 1, here termed the service position, the cup 33 is moved into a part 51 of the rigid neck where the inside diameter is larger. In this position, communication between the bellows 12 and the dispensing head is opened via three orifices 34 which each occupy approximately one third of the cross section of the body 3 between three fins which secure the cup 33 to this body. The liquid contained in the bellows 12 is therefore free to reach an upstream face 62 of the pad 6, via the distribution chamber 31, this requiring only that the user create an overpressure in the flask by action on the bellows 12. In this position, the periphery of the body 3 remains sealed because the two uppermost runs of beading 32 clip into the grooves in the neck 5, while the third (the lowermost one this time) butts against an internal shoulder 53 of this neck.

The dispensing head can be moved between its two different longitudinal positions inside the neck 5, from the security position into the service position, by action on the cap 7 fitted on the assembly, at the time of first use.

The configuration of the cap 7 is apparent from FIGS. 1 and 3. On the inside, in terms of means to collaborate with the nozzle 4 under all circumstances, it has a central pip 71 which engages a short way in the flared end of the conduit 41, an annular ring 72 which guides it and centres it on the external face of a conical extension 43 of the base 42 of the nozzle 4, through which the conduit 41 axially passes, and another annular ring 73 of larger diameter which rests against the outer face of the base 42 on its planar upper face.

The cap 7 can be removed by unscrewing it. However, it is not screwed directly into the neck 5 of the flask but onto the casing 8 mentioned hereinabove. This casing is rigid in all parts. In addition to a main part 81 which forms the case around the bellows 12 it has, as an extension, a neck 82 mounted fixedly on the neck 5 of the flask. It can be seen in FIG. 1 that, for this purpose, the neck 82 and the neck 5 have surfaces with complementing profiles, with shoulders or runs of beading to allow firm engagement by elastic snap-fastening, without there being any need to ensure leaktightness in this region.

On its outer peripheral face, the neck 82 of the casing 8 forms a helical screw thread 84 with which a corresponding screw thread on the interior surface of the cap 7 collaborates. This cap at the outset has a tamperproofing ring 74 which prevents it from being screwed on beyond the security position illustrated in FIG. 3 in which the dish 33 is in sealed contact with the corresponding interior wall of the flask (seat 52) so as to seal the compressible internal volume of the flask.

When the user removes the tamperproofing ring 74, he is then able to screw the cap 7 down into the service position, in which this cap comes into abutment against an upper shoulder 83 of the casing 81. During its longitudinal movement, the cap 7 carries with it the dispensing head 2 and thus pushes it down into the flask until the orifices 34 are opened. Thereafter, the cap can be unscrewed and screwed on for each product-dispensing operation without this moving the dispensing head. It may be pointed out at this point that the casing 8 and the cap 7 advantageously have the same outside diameter, not only to improve the aesthetic appearance but also to make automated manufacture easier.

Returning now to the construction of the dispensing head 2, it may be seen from FIG. 1 that the microporous pad 6 is fitted into the body 3 of the head 2 during assembly when this head has not yet been fitted with the nozzle 4, from the upper opening of its internal cylindrical passage, which has a plane surface, and that it is inserted until it comes into abutment, as appropriate, against an internal shoulder 35.

At its upper end (in the position of FIGS. 1 and 2), the body 3 forms an outer collar 36 which is designed to abut against an upper end either of the neck 5 of the flask or of the neck 82 of the casing 8, when the dispensing head moves from the security position into the service position, at the time of first use. It is onto this collar 36 that the nozzle 4 is assembled, advantageously simply by bonding. Incidentally, but on the inside, this same collar is shaped to incorporate a structure 38 which is moulded as a single piece with it from the material of which the pod body 3 is made, and one of the functions of which is to hold the pad 6 via its downstream face 63.

However, this structure 38, which is very widely open in a star shape, also has the role of forming a spacer between the pad 6 and the base 42 of the nozzle 4. It thus reserves the space for the distribution chamber 31, which it bounds via flared walls between its radial ribs which attach to the cylindrical central part.

Furthermore, via its periphery and via the edge face of its fins, it serves to fix and support the anti-bacterial membrane 9. It could be said that it thus forms one of the membrane support plates, pressing this membrane against the underside of the base 42 of the nozzle 4, which base itself forms the other plate. Annular grooves 44 which prevent continuous contact with the membrane 9 are formed in this base and therefore on the other side of the membrane. Thus, the membrane, bounded and flat between its two support plates, does not remain wetted with solution between two successive dispensing operations, in spite of the effect of its surface tension.

As far as the design of the casing 8 is concerned, the figures illustrate two different embodiments which, however, are identical in the way in which they collaborate with the other parts of the device as illustrated in FIG. 1.

Figure 2B:
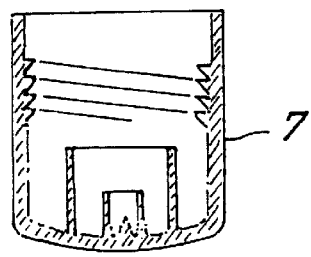
FIG. 2a shows the entire device in its head-down position of use, with its removed cap in FIG. 2b.
Figure 2A:
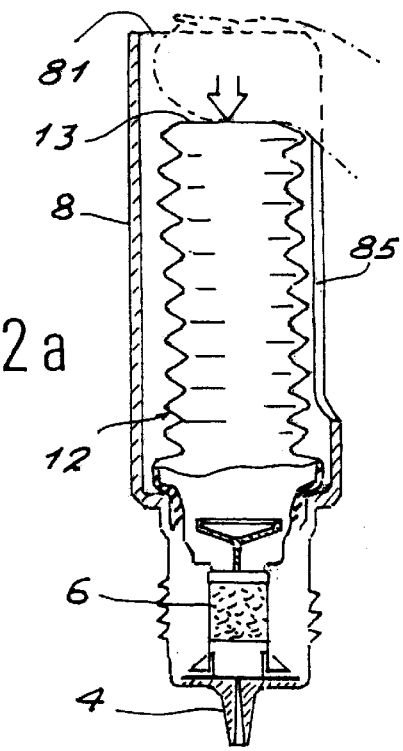

The first of these embodiments is illustrated in FIG. 2a, in a dispensing position with the head down, the cap 7 having been removed by the user (FIG. 2b). In this case, the casing 8 surrounds the bellows 12 over the entire length it has prior to any use. Furthermore, it has no bottom and has a longitudinal slot 85.

To dispense drops, the user slips one finger through this slot to reach the bottom 13 of the bellows, through the open bottom 81 of the casing 8. As the flask empties, there is always sufficient access via the slot 85 for longitudinally compressing the bellows, until only a quantity corresponding to the inevitable dead volume remains.

The second alternative form has the advantage of making better use of the possibilities afforded by the microporous pad 6. Access to the rigid bottom 13 of the bellows is still via an open bottom of the casing 8, but this casing no longer has a longitudinal slot. It therefore has a continuous cylindrical periphery, which leads to greater ease of manufacture since, on an industrial assembly line, labels can easily be stuck on it. The casing 8 is therefore associated with a closure cover 87, designed to close the bottom of the casing around the bellows but, of course, removably.

It goes without saying that the casing 8, with the exclusion of any closure cover 87, is advantageously made as a single piece by the injection-moulding of plastic, using known injection-moulding techniques. The same is true of the flask 1, provided that different wall thicknesses of the same material are envisaged to make sure that the neck 5 and bottom 13 are rigid while giving the rest of the flask sufficient flexibility to allow the flexible bellows 12 to be formed in a post-forming operation.

However, the flask 1 has an unusual particular feature. In this particular instance this is that it has an outer cusp 55 which, at the base of the neck 5, forms a ring which is still rigid, therefore a reinforcing ring, the outer periphery of which protrudes beyond the size of the bellows 12 and in this region forms a planar radial surface. Its usefulness is associated with the method used to assemble the various parts of the device of the invention as will now be described briefly with reference to FIGS. 4 and 5, without detailing those parts of the plant which are conventional in themselves in automated industrial plants, in terms of their construction, relations and functions.

According to these figures, the plant includes a central carousel-type assembly station in which is mounted a turntable 101 able to bring each of four identical cells on its periphery in turn to four work stations arranged around it. It can be seen from FIG. 4 that these work stations comprise three feed stations 102, 103, 104, each consisting, in a way known per se, of a vibrating bowl which receives elements to be assembled from a hopper 105 to make them pass one by one into a chute which presents them in the correct disposition to be picked up by a transfer system which has been given the reference 107. At the fourth work station, the assembly of the device in the cell arriving there is completed; it is then transferred to and collected in a tray 122 for good parts, except for parts which are detected to be poor, which are removed in a reject tray 123.

Each of the feed stations supplies to the assembly station, in turn, during the manufacture of a determined device according to the invention, firstly, the casing 8, which can be seen in FIG. 5 as sitting in the cell 121 (the casing 8 here being of the type with a slot 85), then the flask 1, and finally the end cover 87 which completes the casing of FIG. 3. As an alternative, this third feed station or other work stations added to the turntable could receive elements to assembly such as the cap 7 (which would then be presented on the other side of the turntable), the nozzle 4 or wrappers for packaging.

FIG. 5 shows the installation at the second feed station, the one which corresponds to the handling of the flask on the assembly line, so as to illustrate the usefulness of its reinforcing ring 55.

It can be seen here in particular that the flask 1 is handled head down, while its bellows is protected by a tube 112 which forms part of the transfer system equipment. By contrast, and for reasons concerned with making a very diagrammatic depiction easier to understand, it is only at this stage that it has been revealed in the drawings that the flask is already full of the liquid that is to be marketed and fitted with the pod in which the pad 6 is mounted, that is to say the body 3 of the dispensing head, not yet fitted with the nozzle 4 which will be stuck on from the top at a later stage.

At this stage, benefit is derived from the described design of the device of the invention; with its microporous pad, the body 3 constitutes an effective stopper for the flask as long as the rigid bottom 13 is not pressed to reduce its internal volume and thus create an overpressure with respect to the outside. Sealing is provided by the pad alone, in the rigid neck that extends the flask, by virtue of the elastic compressibility of the pad on its periphery. This then, in combination with the external reinforcing ring 55 of the neck, allows it to be handled head down in the assembly machine. This also allows its security position in the dispensing head to be maintained without it being pushed into the service position.

In effect, the flask 1 is transferred in this position, suspended by a suction effect on its rigid bottom, until it is positioned over the casing 8 already in place in the cell 121. Throughout the time that it is being processed at this work station, its bellows is undeformable because the lower end of the tube 112 is in abutment against the ring 55, more specifically against its rear face which protrudes beyond the bellows. It is also through a mechanical pressing effect exerted on this ring, by the tube 112 engaged with clearance in the casing 8, that the flask is pushed to force its rigid neck 5 into the mouth 82 of the casing 8, this being performed without touching the pod 3 which is in the security position.

The same reinforcing ring 55 can be used, the other way up, to hold the flask using an appropriate gripping tool when the pod is being pushed into its neck as far as this security position.

The above description has been given only by way of an illustrative and nonlimiting example; it is obvious that modifications or variations may be made without in any way departing from the scope of the present invention.

In particular, it was not mentioned hereinabove that the cup 33, moulded as a single piece of the material of the body of the pod 3, is hollowed towards the axis of the device, even though this is clearly evident from the figures. This particular feature improves the flow of liquid towards the pad 6.

Furthermore, in the same region, the three fins which carry this cup (between the passage orifices 34 for the liquid) may, on their upper edge face (FIG. 1) and therefore just downstream of the pad 6, bear a filter which is selective towards one ingredient of the liquid which must not remain in the expelled drops. This would be the case, for example, with an ophthalmic solution containing a preservative which had to be held back by a membrane which filters or purifies by adsorption. It should, however, be noted that the presence of the pad 6 is generally sufficient to provide the necessary effect, according to its material and pore size. In addition, it may be envisaged for it to undergo an appropriate treatment, applying technologies known in themselves, particularly when the pad is made of a felt of unwoven fibres with a density corresponding to low-density polyethylene.

Finally, it may be seen with reference to FIG. 1 that the base 42 of the nozzle 4 has a rim which bounds a bowl in which the membrane 9 is housed. This membrane is thus protected from damage of a mechanical nature until such time as the nozzle is fitted onto the body 3, which at the periphery of the structure 38 has a shape that complements that of this rim.

What is claimed is:

1. A device for packaging a liquid that is to be dispensed drop by drop, comprising a flexible-walled flask (1) that can be deformed manually to gradually decrease its internal volume towards a rigid neck (5) in which is leaktightly mounted a dispensing head (2) ending in a conduit (41) for expelling the liquid out of the flask, characterized in that this device comprises a microporous pad (6) inserted in a body (3) of the said head across the cross-sectional area for the passage of the liquid between said flask (1) and said conduit (41) upstream of a liquid-distribution chamber (31) of large cross-sectional area formed in said body (3) between a downstream surface (63) of said pad (6) and said expulsion conduit (41), said pad (6) being made of a material that is inert with respect to the liquid and capable of creating a head loss which regulates the flow of liquid driven through it by the pressure generated in the flask (1) upon each action to reduce its volume and said distribution chamber (31) having a large enough volume to accommodate the liquid which has passed through said pad (6), said flask (1) being bounded by a wall of cylindrical overall shape in the form of a longitudinally deformable bellows (12) ending in a rigid transverse bottom (13) and being isolated from any possibility of air entering to replace the expelled liquid.

2. A device according claim 1, wherein said bellows (12) is made as a single piece of material that can be molded with said rigid neck (5) for mounting of said dispensing head (2) and with an outer reinforcing ring (52) protruding radially from the overall size of the bellows (12) so as to allow it to be grasped by an automatic assembly machine without touching delicate wall portions of the said bellows.

3. A device according to claim 1, further comprising a downstream filtering element comprising an anti-bacterial membrane (9) inserted between said pad (6) and said conduit (41) across said chamber (31), said membrane being effective in isolating the flask from any possibility of air entering to replace the liquid expelled when this membrane is impregnated with the said liquid.

4. Device according to any one of claims 1 to 3, characterized in that the body (3) of the said dispensing head (2) is mounted so that it can move between two different longitudinal positions inside said neck (5), comprising a security position in which communication between the flask (1) and the said conduit (41) by way of said pad (6) is closed off in a sealed manner and a service position in which there is freedom to communicate with an upstream face (62) of said pad (6) by way of the said distribution chamber (31).

5. Device according to any one of claims 1 to 4, characterized in that the said body (3) of the said dispensing head (2) mounted leaktightly in the said rigid neck (5) has a cylindrical tubular shape, the entire internal cross-sectional area of which is occupied by the said pad over one to two thirds of its length, the remainder being reserved for said distribution chamber (31).

6. A device according to claim 1, wherein said body (3) of said dispensing head (2) mounted leaktightly in the said rigid neck (5) has a cylindrical tubular shape, the entire internal cross-sectional area of which is occupied by said pad over one to two thirds of its length, the remainder being reserved for said distribution chamber (31).

7. A device according to claim 6, wherein said material of the pad (6) is a highly porous open-pore foam or an equivalent felt, forming microducts offered for the passage of the liquid with a mean pore diameter of between 0.3 and 10 microns.

8. A device according to claim 1, further comprising a protective outer casing (8) mounted on said neck and enveloping said flask along a major part of its length.

9. Device according to claim 8, characterized in that the said casing (8) has a continuous cylindrical periphery and is associated with a closure cover (82) which fits onto it as a continuation thereof and is removable to give access to the bottom (13) of the said flask (1).

10. Device according to claim 8, characterized in that the said casing (8) extends over the entire length of the flask (1) and in that it has a longitudinal slot (83) providing access for longitudinally compressing the bellows (12) from its open bottom (81). of the said bellows.

11. Device according to any one of claims 1 to 5, characterized in that the said pad (6) is made of a material based on an organic resin with a slight amount of flexibility to allow it to be forcibly engaged in said body (3) of the dispensing head and thus sealed against it.

12. Device according to claim 11, characterized in that the said material of the pad (6) is a highly porous open-pore foam or an equivalent felt, forming microducts offered for the passage of the liquid with a mean pore diameter of between 0.3 and 10 microns.

13. Device according to any one of claims 1 to 12, comprising a downstream filtering element such as an anti-bacterial membrane according to claim 3, characterized in that the said membrane is supported flat between two perforated plates formed respectively by the said body (3) of the said dispensing head downstream of said distribution chamber (31) and by a nozzle (4) secured thereto and through which the said expulsion conduit (41) is formed.

14. A device according to claim 13, comprising a downstream filtering element comprising an anti-bacterial membrane supported flat between two perforated plates formed respectively by said body (3) of said dispensing head downstream of the said distribution chamber (31) and by a nozzle (4) secured thereto and through which said expulsion conduit (41) is formed.

15. A device for packaging a liquid that is to be dispensed drop by drop, comprising a flexible-walled flask (1) that can be deformed manually to gradually decrease its internal volume towards a rigid neck (5) in which is leaktightly mounted a dispensing head (2) ending in a conduit (41) for expelling the liquid out of the flask, characterized in that this device comprises a microporous pad (6) inserted in a body (3) of the said head across the cross-sectional area for the passage of the liquid between said flask (1) and said conduit (41) upstream of a liquid-distribution chamber (31) of large cross-sectional area formed in said body (3) between a downstream surface (63) of said pad (6) and said expulsion conduit (41), said pad (6) being made of a material that is inert with respect to the liquid and capable of creating a head loss which regulates the flow of liquid driven through it by the pressure generated in the flask (1) upon each action to reduce its volume and said distribution chamber (31) having a large enough volume to accommodate the liquid which has passed through said pad (6), said flask (1) being bounded by a wall of cylindrical overall shape in the form of a longitudinally deformable bellows (12) ending in a rigid transverse bottom (13) and being isolated from any possibility of air entering to replace the expelled liquid, further comprising a downstream filtering element comprising an anti-bacterial membrane (9) inserted between said pad (6) and said conduit (41) across said chamber (31), said membrane being effective in isolating the flask from any possibility of air entering to replace the liquid expelled when this membrane is impregnated with the said liquid.

16. A device for packaging a liquid that is to be dispensed drop by drop, comprising a flexible-walled flask (1) that can be deformed manually to gradually decrease its internal volume towards a rigid neck (5) in which is leaktightly mounted a dispensing head (2) ending in a conduit (41) for expelling the liquid out of the flask, characterized in that this device comprises a microporous pad (6) inserted in a body (3) of the said head across the cross-sectional area for the passage of the liquid between said flask (1) and said conduit (41) upstream of a liquid-distribution chamber (31) of large cross-sectional area formed in said body (3) between a downstream surface (63) of said pad (6) and said expulsion conduit (41), said pad (6) being made of a material that is inert with respect to the liquid and capable of creating a head loss which regulates the flow of liquid driven through it by the pressure generated in the flask (1) upon each action to reduce its volume and said distribution chamber (31) having a large enough volume to accommodate the liquid which has passed through said pad (6), said flask (1) being bounded by a wall of cylindrical overall shape in the form of a longitudinally deformable bellows (12) ending in a rigid transverse bottom (13) and being isolated from any possibility of air entering to replace the expelled liquid, and wherein the body (3) of said dispensing head (2) is mounted so that it can move between two different longitudinal positions inside the said neck (5), comprising a security position in which communication between the flask (1) and said conduit (41) by way of the said pad (6) is closed off in a sealed manner and a service position in which there is freedom to communicate with an upstream face (62) of said pad (6) by way of said distribution chamber (31).

17. A device for packaging a liquid that is to be dispensed drop by drop, comprising a flexible-walled flask (1) that can be deformed manually to gradually decrease its internal volume towards a rigid neck (5) in which is leaktightly mounted a dispensing head (2) ending in a conduit (41) for expelling the liquid out of the flask, characterized in that this device comprises a microporous pad (6) inserted in a body (3) of the said head across the cross-sectional area for the passage of the liquid between said flask (1) and said conduit (41) upstream of a liquid-distribution chamber (31) of large cross-sectional area formed in said body (3) between a downstream surface (63) of said pad (6) and said expulsion conduit (41), said pad (6) being made of a material that is inert with respect to the liquid and capable of creating a head loss which regulates the flow of liquid driven through it by the pressure generated in the flask (1) upon each action to reduce its volume and said distribution chamber (31) having a large enough volume to accommodate the liquid which has passed through said pad (6), said flask (1) being bounded by a wall of cylindrical overall shape in the form of a longitudinally deformable bellows (12) ending in a rigid transverse bottom (13) and being isolated from any possibility of air entering to replace the expelled liquid, and wherein said body (3) of said dispensing head (2) mounted leaktightly in the said rigid neck (5) has a cylindrical tubular shape, the entire internal cross-sectional area of which is occupied by said pad over one to two thirds of its length, remainder being reserved for the said distribution chamber (31).

18. A device for packaging a liquid that is to be dispensed drop by drop, comprising a flexible-walled flask (1) that can be deformed manually to gradually decrease its internal volume towards a rigid neck (5) in which is leaktightly mounted a dispensing head (2) ending in a conduit (41) for expelling the liquid out of the flask, characterized in that this device comprises a microporous pad (6) inserted in a body (3) of the said head across the cross-sectional area for the passage of the liquid between said flask (1) and said conduit (41) upstream of a liquid-distribution chamber (31) of large cross-sectional area formed in said body (3) between a downstream surface (63) of said pad (6) and said expulsion conduit (41), said pad (6) being made of a material that is inert with respect to the liquid and capable of creating a head loss which regulates the flow of liquid driven through it by the pressure generated in the flask (1) upon each action to reduce its volume and said distribution chamber (31) having a large enough volume to accommodate the liquid which has passed through said pad (6), said flask (1) being bounded by a wall of cylindrical overall shape in the form of a longitudinally deformable bellows (12) ending in a rigid transverse bottom (13) and being isolated from any possibility of air entering to replace the expelled liquid, further comprising a downstream filtering element comprising an anti-bacterial membrane supported flat between two perforated plates formed respectively by said body (3) of said dispensing head downstream of the said distribution chamber (31) and by a nozzle (4) secured thereto and through which said expulsion conduit (41) is formed.

19. A device for packaging a liquid that is to be dispensed drop by drop, comprising a flexible-walled flask (1) that can be deformed manually to gradually decrease its internal volume towards a rigid neck (5) in which is leaktightly mounted a dispensing head (2) ending in a conduit (41) for expelling the liquid out of the flask, characterized in that this device comprises a microporous pad (6) inserted in a body (3) of the said head across the cross-sectional area for the passage of the liquid between said flask (1) and said conduit (41) upstream of a liquid-distribution chamber (31) of large cross-sectional area formed in said body (3) between a downstream surface (63) of said pad (6) and said expulsion conduit (41), said pad (6) being made of a material that is inert with respect to the liquid and capable of creating a head loss which regulates the flow of liquid driven through it by the pressure generated in the flask (1) upon each action to reduce its volume and said distribution chamber (31) having a large enough volume to accommodate the liquid which has passed through said pad (6), said flask (1) being bounded by a wall of cylindrical overall shape in the form of a longitudinally deformable bellows (12) ending in a rigid transverse bottom (13) and being isolated from any possibility of air entering to replace the expelled liquid, and wherein said pad (6) is made of a material based on an organic resin with a slight amount of flexibility to allow it to be forcibly engaged in said body (3) of the dispensing head and thus sealed against it.

20. A device according to claim 19, wherein said material of the pad (6) is a highly porous open-pore foam or an equivalent felt, forming microducts offered for the passage of the liquid with a mean pore diameter of between 0.3 and 10 microns.

* * * * *